(12) United States Patent
Jayaraman

(10) Patent No.: US 6,641,611 B2
(45) Date of Patent: Nov. 4, 2003

(54) THERAPEUTIC COATING FOR AN INTRAVASCULAR IMPLANT

(76) Inventor: Swaminathan Jayaraman, 459 Lowell Pl., Fremont, CA (US) 94536

( * ) Notice: Subject to any disclaimer, the term of this patent is extended or adjusted under 35 U.S.C. 154(b) by 0 days.

(21) Appl. No.: 09/994,253

(22) Filed: Nov. 26, 2001

(65) Prior Publication Data

US 2003/0099712 A1 May 29, 2003

(51) Int. Cl.$^7$ .................................................. A61F 2/06
(52) U.S. Cl. ..................... 623/1.42; 623/1.11; 424/400; 424/422; 424/423
(58) Field of Search ................................ 424/400, 422, 424/423; 623/1.11, 1.42; 427/2.1

(56) References Cited

U.S. PATENT DOCUMENTS

| | | |
|---|---|---|
| 3,903,071 A | 9/1975 | Holmes |
| 4,650,803 A | 3/1987 | Stella et al. |
| 5,100,899 A | 3/1992 | Calne |
| 5,212,155 A | 5/1993 | Calne |
| 5,221,740 A | 6/1993 | Hughes |
| 5,282,785 A | 2/1994 | Shapland et al. |
| 5,283,257 A | 2/1994 | Gregory et al. |
| 5,286,254 A | 2/1994 | Shapland et al. |
| 5,286,731 A | 2/1994 | Caufield et al. |
| 5,288,711 A | 2/1994 | Mitchell et al. |
| 5,308,847 A | 5/1994 | Calne |
| 5,318,895 A | 6/1994 | Kahn et al. |
| 5,403,833 A | 4/1995 | Calne |
| 5,457,113 A | 10/1995 | Cullinan et al. |
| 5,461,058 A | 10/1995 | Calne |
| 5,496,832 A | 3/1996 | Armstrong |
| 5,508,397 A | 4/1996 | Or et al. |
| 5,516,781 A * | 5/1996 | Morris et al. ............... 514/291 |
| 5,519,042 A | 5/1996 | Morris et al. |
| 5,624,946 A | 4/1997 | Williams |
| 5,646,160 A | 7/1997 | Morris et al. |
| 5,674,732 A | 10/1997 | Nishida et al. |
| 5,688,824 A | 11/1997 | Williams |
| 5,728,710 A | 3/1998 | Luengo |
| 5,837,313 A | 11/1998 | Ding et al. |
| 5,891,507 A | 4/1999 | Javaraman |
| 5,997,468 A | 12/1999 | Wolff et al. |

(List continued on next page.)

FOREIGN PATENT DOCUMENTS

| | | |
|---|---|---|
| WO | WO 96/04906 A1 | 2/1996 |
| WO | WO 98/07415 A2 | 2/1998 |
| WO | WO 98/18468 A1 | 5/1998 |
| WO | WO 98/55162 A2 | 12/1998 |

OTHER PUBLICATIONS

M. Guba et al., Rapamycin inhibits primary and metastatic tumor growth by angiogenesis: involvement of vascular endothelial growth factor, Nature Medicine, vol. 8, Feb. 2002, pp 128–135.

(List continued on next page.)

*Primary Examiner*—Michael G. Hartley
*Assistant Examiner*—Konata M George
(74) *Attorney, Agent, or Firm*—Fleit, Kain, Gibbons, Gutman and Bongini; Paul D. Bianco; Martin Fleit

(57) ABSTRACT

The invention relates to a coating for an intravascular implant that prevents hyperproliferative vascular disease after a mechanical injury, such as angioplasty. The coating includes first and second agents, with the first agent acting on a calcium independent cellular pathway and the second agent acting on a calcium dependent cellular pathway. In an exemplary embodiment, the first agent is rapamycin and the second agent is cyclosporine A. The agents can be incorporated in a polymeric agent and can be applied either directly to the implant or on top of a primer layer placed on the implant. A top coat can be applied to the therapeutic coating, if desired.

25 Claims, 5 Drawing Sheets

U.S. PATENT DOCUMENTS

| | | | |
|---|---|---|---|
| 6,046,328 A | 4/2000 | Schonharting et al. | |
| 6,051,596 A | 4/2000 | Badger | |
| 6,071,305 A | 6/2000 | Brown et al. | |
| 6,129,705 A | 10/2000 | Grantz | |
| 6,143,037 A | 11/2000 | Goldstein et al. | |
| 6,153,252 A | 11/2000 | Hossainy et al. | |
| 6,197,781 B1 | 3/2001 | Guitard et al. | |
| 6,203,551 B1 | 3/2001 | Wu | |
| 6,231,600 B1 | 5/2001 | Zhong | |
| 6,238,430 B1 | 5/2001 | Klumb et al. | |
| 6,239,102 B1 | 5/2001 | Tiemessen | |
| 6,239,124 B1 * | 5/2001 | Zenke et al. | 514/183 |
| 6,248,127 B1 | 6/2001 | Shah et al. | |
| 6,251,136 B1 | 6/2001 | Guruwaiya et al. | |
| 6,254,634 B1 | 7/2001 | Anderson et al. | |
| 6,258,121 B1 | 7/2001 | Yang et al. | |
| 6,273,913 B1 * | 8/2001 | Wright et al. | 623/1.42 |
| 6,335,029 B1 | 1/2002 | Kamath et al. | |
| 6,344,035 B1 | 2/2002 | Chudzik et al. | |
| 6,364,903 B2 | 4/2002 | Tseng et al. | |
| 6,368,658 B1 | 4/2002 | Schwarz et al. | |
| 6,379,382 B1 | 4/2002 | Yang | |
| 2001/0008888 A1 | 7/2001 | Zenke et al. | |
| 2001/0027340 A1 | 10/2001 | Wright et al. | |
| 2001/0029351 A1 | 10/2001 | Falotico et al. | |
| 2002/0005206 A1 | 1/2002 | Falotico et al. | |
| 2002/0007213 A1 | 1/2002 | Falotico et al. | |
| 2002/0007214 A1 | 1/2002 | Falotico et al. | |
| 2002/0007215 A1 | 1/2002 | Falotico et al. | |
| 2002/0013335 A1 | 1/2002 | Azrolan et al. | |
| 2002/0016625 A1 | 2/2002 | Falotico et al. | |

OTHER PUBLICATIONS

M. Iurlaro et al., Antiangiogenesis by cyclosporine. Experimental Hematology, vol. 26, 1998, pp. 1215–1222.

D. Bunjes, C. Hardt, M Willinghoff and H Wagner, Cyclosporin A Mediates Immunosuppression of Primary Cytotoxic T Cell Responses by Impairing the Release of Interleukin 1 and Interleukin 2, J. Immunol. 1981, 11:657–661.

J DiJoseph, E Fluhler, J Armstrong, M Sharr, and S Sehgal, Therapeutic Blood Levels of Sirolimus (Rapamycin) in the Allografted Rat, Transplantation 1996, 62: 1109–1112.

B Hausen, K Boeke, G Berry, I Begarra, L Benet, U Christians and R Morris, Coadministration of Neoral and the Novel Rapamycin Analog, SDZ RAD, to Rat Lung Allograft Recipients, Transplantation 1999, 67:956–962.

L Turka, J Dayton, G Sinclair, C Thompson, and B Mitchell, Guanine Ribonucleotide Depletion Inhibits T Cell Activation, J. Clin. Invest. 1991, 87:940–948.

W Schuler, R Sedrani, S Cottens, B Haberlin, M. Schulz, H Schuurman, G Zenker, H Zerwes, and M Schreiber, SDZ RAD, a New Rapamycin Derivative. Transplantation 1997, 64:36–42.

H Schuurman, J Ringers, W Schuler, W Slingerland and M Jonker, Oral Efficacy of the Macrolide Immunosuppressant SDZ RAD and of Cyclosporine Microemulsion in Cynomolgus Monkey Kidney Allotransplantation, Transplantation 2000, 69:737–742.

J. Sousa, A Abizaid, A Abizaid, F Feres, I Pinto, A Seixas, R Staico, L Mattos, A Sousa, R Falotico, J Jaeger, J Popma, P Serruys, M Costa, Lack of Neointimal Proliferation after Implantation of Sirolimus–Coated Stents in Human Coronary Arteries, Circulation 2000, 102:r54–r57.

C Gregory, S Katznelson, S Griffey, A Kyles and E Berryman, Fluvastatin in Combination with RAD Signicantly Reduces Graft Vascular Disease in Rat Cardiac Allografts, Circulation 2001, 72:989–993.

R Morris, Immunopharmacology of New Xenobiotic Immunosuppressive Molecules, Seminars in Nephrology 1992, 12:304–314.

J Mehilli, A Kastrati, W Koch, C Bottiger, N Von Beckerath, A Schomig, Relation Between Tumor Necrosis Factor (TNF) Gene Polymorphisms and Thrombotic Events and Restenosis in Patients with Coronary Stenting, Abstract From ACCIS 2000 Meeting, 13A.

R. Knight, M. Ferraresso, F. Serino, S. Katz, R. Lewis, and B.D. Kahan, Low–Dose Rapamycin Potentiates the Effects of Subtherapeutic Doses of Cyclosporine to Prolong Renal Allograft Survival in the Mongrel Canine Model, Transplantation 1993, 55:947–949.

H Schuurman, S Cottens, S Fuchs, J Joergensen, T Meerloo, R Sedrani, M Tanner, G Zenke and W Schuler, SDZ RAD, A New Rapamycin Derivative, Transplantation 1997, 64:32–35.

B Kahan, M Murgia, J Slation, and dK Napoli, Potential Applications of Therapeutic Drug Monitoring of Sirolimus Immunosuppression in Clinical Renal Transplantation, Therapeutic Drug Monitoring 1995, 17:672–675.

R Yatscoff, P Wang, K Chan, D Hicks and J Zimmerman, Rapamycin: Distribution, Pharmacokintetics, and Therapeutic Range Investigations, Therapeutic Drug Monitoring 1995, 17:666–671.

H.U. Schorlemmer, F.R. Seiler, and R.R. Bartlett, Prolongation of Allogeneic Transplantation Skin Grafts and Induction of Tolerance by Leflunomide, a New Immunosuppressive Isoxazol Derivative, Transplantation Proceedings 1993, 25:753–767.

D Branisteanu, C Mathieu, R Bouillon, Synergism Between Sirolimus and 1.25 Dihyhdroxyvitamin D, in Vitro and in Vivo, Journal of Neuroimmunology 1979, 79:138–147.

B Kahan, Efficacy of Sirolimus Compared with Azathioprine for Reduction of Acute Renal Allograft Rejection: A Randomised Multicentre Study, Lancet 2000, 356:194–202.

B Klugherz, G Llanos, W Lieuallen, G. Kopla, G Papandreou, P Narayan, T Levengood, B Sasseen, S Adelman, R Falotico, R Wileneir, Stent–Based Delivery of Sirolimus for the Prevention of Restenosis, Abstract from ACCIS 2000 Meeting.

R Saunders, M Metcalfe, M Nicholson, Rapamycin in Transplantation, a Review of Evidence, Kidney International 2001, 59:3–16.

R Yatschoff, D LeGatt, and N Kneteman, Therapeutic Monitoring of Rapamycin: a New Immunosuppressive Drug, Therapeutic Drug Monitoring 1993, 15:478–482.

S Stepkowski, K Napoli, M Wang, X Qu, T Chou, and B Kahan, Effects of the Pharmacokinetic Interaction Between Orally Administered Sirolimus and Cyclosporine on the Synergistic Prolongation of Heart Allograft Survival in Rats, Transplantation 1996, 62:986–994.

B. Hausen, J. Gummert, G.J. Berry, U.Christians, N. Serkova, T. Ikonen, L. Hook, F. Legay, W. Schuler, M.H. Schreier, and R.E. Morris, Prevention of Acute Allograft Rejection in Nonhuman Primate Lung Transplant Recipients, Transplantation 2000, 69:488–496.

S Sehgal, Rapumune (Sirolumus, Rapamycin): An Overview and Mechanism of Action, Therapeutic Drug Monitoring 1995, 17:660–665.

R Morris, Mechanisms of Action of New Immunosuppressive Drugs, Therapeutic Drug Monitoring 1995, 17:564–569.

P Kelly, S Gruber, F Behbod, and B Kahan, Sirolimus, a New, Potent Immunosuppressive Agent, Pharmacotherapy 1997, 17:1148–1156.

G Ingle, T Stevens, and C Holt, Sirolimus: Continuing the Evolution of Transplant Immunosuppression, The Annals of Pharmacotherapy 2000, 34:1044–1055.

S Marx, A Marks, Bench to Bedside, The Development of Rapamycin and its Application of Stent Restenosis, Circulation 2001, 104:852–855.

S.M. Stepkowski and B.D. Kahan, Synergistic Activity of the Triple Combination: Cyclosporine, Rapamycin, and Brequinar, Transplantation Proceedings 1993, 24:29–31.

B Kahan, M Murgia, J Slaton, and K Napoli, Potential Applications of Therapeutic Drug Monitoring of Sirolimus Immunosuppression in Clinical Renal Transplantation, Therapeutic Drug Monitoring 1995. 17:672–675.

S Sehgal, Rapamune (RAPA, Rapamycin, Sirolumus): Mechanism of Action Immunosuppressive Effect Results from Blockade of Signal Transduction and Inhibition of Cell Cycle Progression, Clinical Biochemistry 1998, 31:335–351.

B Kahah, J Chang, S Sehgal, Preclinical Evaluation of a New Potent Immunosuppressive Agent, Rapamycin, Transplantation 1991, 52:185–191.

O Vilicky, H Zou, V Muller, J Lacha, A Szabo and U Heemann, SDZ–RAD Prevents Manifestation of Chronic Rejection in Rat Renal Allografts, Transplantation 2000, 69:497–502.

K Napoli and B Kahan, High–Performance Liquid Chromatography of Rapamycin, Clinical Chemistry 1991, 37:294–295.

Henderson, D.J., Naya, R. V. Bundick, G.M. Smith and G. A. Schmidt, 1991. Comparison of the effects of FK–506, Cyclosporin–A, and rapamycin on IL–2 production. Immunology 73:316.

Vathsala, A., T.C. Chou, B.D. Kahan, 1990. Analysis of the interactions of immunosuppressive drugs with cyclosporine in inhibiting DNA proliferation. Transplantation 49: 463.

Kahan B.D., S. Gibbons, N. Tejpal, S.M. Stepkowski and T.C. Chou. 1991. Synergistic interactions of cyclosporine and rapamycin to inhibit immune performances of normal human peripheral blood lymphocytes in vitro. Transplantation 51: 232.

Tu, Y, Stepkowski SM, Chou TC, Kahan BD. The synergistic effects of cyclosporine, sirolimus and brequinar on heart allograft survival in mice. Transplantation 1995; 59: 177.

Martin DF, DeBarge LR, Nussenblatt RB, Chan CC, Roberge FG. Synergistic effect of rapamycin and cyclosporin A in the treatment of experimental autoimmune uveoretinitis. J Immunol 1995; 154: 922.

Yakimets WJ, Lakey JR, Yatscoff RW, et al. Prolongation of canine pancreatic islet allograft survival with combined rapamycin and cyclosporine therapy at low does: rapamycin efficacy is blood level related. Transplantation 1993; 56: 1293.

Gregory CR, Huang X, Pratt RE, et al. Treatment with rapamycin and mycophenolic acid reduces arterial intimal thickening produced by mechanical injury and allows endothelial replacement. Transplantation. 1995; 59: 655–661.

Gallo R, Padurean A, Jayaraman T. et al. Inhibition of intimal thickening after balloon angioplasty in porcine coronary arteries by targeting regulators of cell cycle. Circulation, 1999; 99: 2164–2170.

Reddy, KR, Controlled–Release, Pegylation, Liposomal Formulations: New Mechanisms in the Delivery of Injectable Drugs, The Annals of Pharmacotherapy, vol. 34, pp 915–923, Jul./Aug. 2000.

* cited by examiner

THERAPEUTIC COATING FOR AN INTRAVASCULAR IMPLANT

FIELD OF THE INVENTION

The present invention relates to a therapeutic coating for an intravascular implant, and in particular to a coating that prevents or treats hyperproliferative vascular disease including intimal smooth muscle cell hyperplasia, restenosis, and vascular occlusion.

BACKGROUND OF THE INVENTION

As discussed in more detail below, the prior art discloses many examples of therapeutic coatings that have been applied to intravascular devices. The objective behind applying the therapeutic coating is to either mediate or suppress a tissue response at the site of implantation. For example in intravascular situations, one of the obvious outcomes of implanting a foreign body is for an intense reaction at the site of implantation. This intense reaction can result from either the implantation itself or the stresses generated after implantation. Due to the reaction, there is an obvious interaction by the vessel wall to compensate for this injury by producing a host of tissue related responses that is generally called "healing due to injury." It is this healing process that the therapeutic coating attempts to mediate, suppress, or lessen. In some instances, this healing process is excessive in which it occludes the entire lumen providing for no blood flow in the vessel. This reoccluded vessel is also called a resteinotic vessel.

Therapeutic coatings can behave in different ways. For example, depending upon the kind of therapeutic agent used, the various cellular levels of mechanisms are tackled. Some of the therapeutic agents act on the growth factors that are generated at the site of implantation or intervention of the vessel. Some other therapeutic agents act on the tissues and suppress the proliferative response of the tissues. Others act on the collagen matrix that comprises the bulk of the smooth muscle cells. Some examples of prior art relating to therapeutic coatings follow.

U.S. Pat. No. 5,283,257 issued to Gregory et al. provides a method of preventing or treating hyperproliferative vascular disease in a mammal by administering an amount of mycophenolic acid effective to inhibit intimal thickening. This drug can be delivered either after angioplasty or via a vascular stent that is impregnated with mycophenolic acid.

U.S. Pat. No. 5,288,711 issued to Mitchell et al. provides a method of preventing or treating hyperproliferative vascular disease in a mammal by administering an antiproliferative effective amount of a combination of rapamycin and heparin. This combination can be delivered either after angioplasty or via a vascular stent that is impregnated with the combination.

U.S. Pat. Nos. 5,516,781 and 5,646,160 issued to Morris et al. disclose a method of preventing or treating hyperproliferative vascular disease in a mammal by administering an antiproliferative effective amount of rapamycin alone or in combination with mycophenolic acid. The rapamycin or rapamycin/mycophenolic acid combination can be delivered via a vascular stent.

U.S. Pat. No. 5,519,042 issued to Morris et al. teaches a method of preventing or treating hyperproliferative vascular disease in a mammal consists of administering to a mammal an effective amount of carboxyamide compounds. This can also be delivered intravascularly via a vascular stent.

U.S. Pat. No. 5,646,160 issued to Morris et al. provides a method of preventing or treating hyperproliferative vascular disease in a mammal by administering an antiproliferative effective amount of rapamycin alone or in combination with mycophenolic acid. This can be delivered intravascularly via a vascular stent.

Each of the above-identified patents utilizes an immunosuppressive agent. Since the mid 1980's, many new small molecular weight molecules of natural product, semi-synthetic or totally synthetic origin have been identified and developed for the control of graft rejection. These include mizoribine, deoxysperguzalin, cyclosporine, FK 506, mycophenolic acid (and its prodrug form as mycophenolate mofetil), rapamycin, and brequinar sodium. The mechanisms of some of these agents will now be briefly summarized.

Both cyclosporine and FK 506 suppress T-cell activation by impeding the transcription of selected cytokine genes in T cells. Neither has any known direct effects on B cells. The suppression of interleukin 2 (IL-2) synthesis is an especially important effect of these two agents, because this cytokine is required for T cells to progress from initial activation to DNA synthesis. Both cyclosporine A and FK 506 bind to cytoplasmic proteins. It has been recently proposed that cyclosporine A and FK 506 are bifunctional: one segment of the immunosuppressant molecule is responsible for binding to the rotamase and, once bound, a separate part of the molecule interacts with a cytoplastmic phosphatase (calcineurin) and causes the phosphatase to become inactive or have altered specificity. Unlike all previously developed immunosuppressants and even the most recent xenobiotic immunosuppressants, FK 506 is the only compound in the history of immunosuppressive drug development that is the product of a drug discovery program designed specifically to identify an improved molecule for the control of allograft rejection. Every other past and "new" immunosuppressive xenobiotic drug is the unanticipated result of drug discovery programs organized to identify lead compounds for anticancer, anti-inflammatory, or antibiotic therapy.

Neither cyclosporine, FK 506, rapamycin nor other immunosuppressants are the product of evolutionary pressures that led to our current use of them as immunosuppressants. The agents are fungal (cyclosporine A) or bacterial (FK 506, rapamycin) metabolites that suppress lymphocyte proliferation purely through coincidental molecular interactions. Therefore, as our ability to design drugs that perform specific intravascular functions increases, there should be a reciprocal decrease in the severity of their adverse effects.

There is a need for safer versions of cyclosporine, FK 506, rapamycin and mycophenolic acid as well as for analogues with higher immunosuppressive efficacy. Because of their toxicities, these agents cannot be used at maximally immunosuppressive doses. Our understanding of the molecular basis of toxic effects of these agents is far less clear than their proposed mechanisms of action on T cells. Until we can combine an understanding of the molecular mechanisms responsible for both the agent's immunosuppressive actions and its toxic effects, it will be difficult to use rational drug design to limit an agent's effects solely to suppression of T cell activation.

The other significant issue that complicates the delivery of relatively high dosage of the agents is the relatively narrow therapeutic window. This narrow window of therapeutic vs. toxicity restricts most of these agents to be used as monotherapy for intravascular delivery.

Rapamycin, for example, inhibits the IL-2 induced proliferation of specific IL-2 responsive cell lines, but neither cyclosporine nor other drugs can suppress this response. Because rapamycin acts late in the activation sequence of T cells, it also effectively inhibits T cells inactivated by a recently described calcium independent pathway. Thus, T cells stimulated through this alternative route are insensitive to suppression by cyclosporine A and FK 506, but rapamycin inhibits their proliferation only.

The toxicity profile of rapamycin resembles cyclosporine A and FK 506. Rapamycin is associated with weight loss in several species, and treatment with high does of rapamycin causes diabetes in rats, but not in nonhuman primates. Initial animal data suggests that rapamycin may be less nephrotoxic than cyclosporine A, but its effects on kidneys with impaired function have not been evaluated. Rapamycin at highly effective therapeutic doses is highly toxic and its usage is recommended along with a combination of other immunosuppressants. The combination with cyclosporine A results in a significant increase in the therapeutic level in blood when compared with monotherapy. A lower dosage of the combination is more effective than a higher dosage of monotherapy. The dosage of rapamycin could be reduced nine fold and cyclosporine A could be reduced five fold when these agents are used in combination. In addition, the combination is also not toxic. In fact, the U.S. FDA has approved the usage of rapamycin for transplantation and allograft rejection only upon combination therapy with cyclosporine.

In summary, the problems associated with immunosuppressive agents include, narrow therapeutic window, toxicity window, inefficacy of agents, and dosage related toxicity. In order to overcome these problems, combination therapy involving two agents has been used with success. It has been surprisingly found that the benefits of combined immunosuppression with rapamycin and cyclosporine A have a very synergistic approach towards cellular growth and retardation. Studies have shown that suppression of heart graft rejection in nonhuman primates is especially effective when rapamycin is combined with cyclosporine A. The immunosuppressive efficacy of combined therapy is superior to treatment with either agent alone; this effect is not caused by the elevation of cyclosporine A blood levels by co-administration of rapamycin. The combination treatment with rapamycin and cyclosporine A does not cause nephrotoxicity. The distinct sites of immunosuppressive action of cyclosporine A and rapamycin (cyclosporine A acts on the calcium dependent and rapamycin acts on the calcium independent pathway) and their relatively non-overlapping toxicities will enable this combination to be used intravascularly to prevent cellular growth at the site of injury inside the blood vessel after angioplasty.

Several scientific and technical publications mention the "surprisingly" "synergistic" effect of rapamycin and cyclosporine A. These include:

Schuurman et al. in Transplantation Vol 64, 32–35, No. 1, Jul. 15, 1997 describe SDZ-RAD, a new rapamycin derivative that has a synergism with cyclosporine. They conclude that both the drugs show synergism in immunosuppression, both in vitro and in vivo. The drugs are proposed to have a promising combinatorial therapy in allotransplantation.

Schuler et al. in Transplantation Vol 64, 36–42, No. 1, Jul. 15, 1997 report that the drug rapamycin by itself has a very narrow therapeutic window, thus decreasing its clinical efficacy. They reported that in combination with cyclosporine A, the drugs act in a synergistic manner. This synergism, if proven in humans, offers the chance to increase the efficacy of the immunosuppressive regimen by combining the two drugs, with the prospect of mitigating their respective side effects. The authors also propose that they believe that the increased immunosuppressive efficacy of a drug combination composed of cyclosporine A and rapamycin, combined with the ability of rapamycin to prevent VSMC proliferation, bears the potential for improving the prospects for long term graft acceptance.

Morris et al. in Transplantation Proceedings, Vol 23, No. 1 (February), 1991: pp. 521–524 describe the synergistic activity of cyclosporine A and rapamycin for the suppression of alloimmune reactions in vivo.

Schuurman et al. in Transplantation Vol 69, 737–742, No. 5, Mar. 15, 2000 describe the oral efficacy of the macrolide immunosuppressant rapamycin and of cyclosporine microemulsion in cynomalgus monkey kidney allotransplantation. The authors describe the synergistic activity of both these combinations and explain the possible explanation for failure of rapamycin monotherapy to ensure long term survival in this animal model might be the different mode of action of the compound when compared to cyclosporine. Cyclosporine acts very early in the chain of events that lead to a T-cell immune response. It blocks the antigen-driven activation of T cells, inhibiting the production of early lymphokines by interfering with the intracellular signal that emanates from the T-cell receptor upon recognition of antigen. Rapamycin acts rather late after T cell activation. The authors conclude that drugs like rapamycin need to be combined with immunosuppressants like cyclosporine to inhibit the early T-cell activation event and thus prevent an inflammatory response.

Hausen et al. in Transplantation Vol 69, 488–496, No. 4, Feb. 27, 2000 describe the prevention of acute allograft rejection in nonhuman primate a lung transplant recipients. The authors mention that fixed dose studies using monotherapy with either high dose cyclosporine A or a high dose rapamycin did not prevent early acute allograft rejection, but monotherapy with either drug was well tolerated. The fixed doses of the drugs were used in combination, but this led to 5 fold increase in rapamycin levels compared to levels in monkeys treated with rapamycin alone. To compensate for this adverse drug-drug interaction, concentration controlled trials were designed to lower rapamycin levels and cyclosporine A levels considerably when both the drugs were used together. This specimen suppressed rejection successfully.

Martin et al. in the Journal of Immunology in 1995 published a paper "Synergistic Effect of Rapamycin and cyclosporine A in the Treatment of Experimental Autoimmune Uveoretinitis". The authors conclude that immunosuppressive drugs currently available for the treatment of autoimmune diseases display a narrow therapeutic window between efficacy and toxic side effects. The use of combination of drugs that have a synergistic effect may expand this window and reduce the risk of toxicity. The studies demonstrated synergistic relationship between rapamycin and cyclosporine A and the combination allows the use of reduced does of each drug to achieve a therapeutic effect. The use of lower does may also reduce the toxicity of these drugs for the treatment of autoimmune uveitis.

Henderson et al. in immunology 1991, 73: 316–321 compare the effects of rapamycin and cyclosporine A on the IL-2 production. While rapamycin did not have any effect on the IL-2 gene expression, cyclosporine A did have an effect on the IL-2 gene expression. This shows that the two drugs have a completely different pathway of action.

Hausen et al. in Transplantation Vol 67, 956–962, No. 7, Apr. 15, 1999 published the report of co administration of Neural (cyclosporine A) and the novel rapamycin analog (SDZ-RAD), to rat lung allograft recipients. They mention the synergistic effect of the two compounds—cyclosporine A inhibits early events after T-cell activation, rapamycin affects growth factor driven cell proliferation. Simultaneous administration of cyclosporine A and rapamycin has shown to result in significant increases in rapamycin trough (levels of the drug in blood) when compared with monotherapy. In preclinical and clinical trials, the immunosuppressive strategies have been designed to take advantage of the synergistic immunosuppressive activities of cyclosporine A given in combination with rapamycin. In addition to immunosuppressive synergism, a significant pharmacokinetic interaction after simultaneous, oral administration of cyclosporine A and rapamycin has been found in animal studies.

Whiting et al. in Transplantation Vol 52, 203–208, No. 2, August 1991 describe the toxicity of rapamycin in a comparative and combination study with cyclosporine at immunotherapeutic dosage in the rat.

Yizheng Tu et al. in Transplantation Vol 59, 177–183, No. 2 Jan. 27, 1995 published a paper on the synergistic effects of cyclosporine, Siolimus (rapamycin) and Brequinar on heart allograft survival in mice.

Yakimets et al. in Transplantation Vol 56, 1293–1298, No. 6, December 1993 published the "Prolongation of Canine Pancreatic Islet Allograft Survival with Combined rapamycin and cyclosporine Therapy at Low Doses".

Vathsala et al. in Transplantation Vol 49, 463–472, No. 2, February 1990 published the "Analysis of the interactions of Immunosuppressive drugs with cyclosporine in inhibiting DNA proliferation".

The combination of rapamycin and cyclosporine A, delivered by a variety of mechanisms, has been patented for the treatment of many diseases. The patent literature is summarized below:

U.S. Pat. No. 5,100,899 issued to Calne provides a method of inhibiting organ or tissue transplant rejection in a mammal. The method includes administering to the mammal a transplant rejection inhibiting amount of rapamycin. Also disclosed is a method of inhibiting organ or tissue transplant rejection in a mammal that includes administering (a) an amount of rapamycin in combination with (b) an amount of one or more other chemotherapeutic agents for inhibiting transplant rejection, e.g., azathiprine, corticosteroids, cyclosporine and FK 506. The amounts of (a) and (b) together are effective to inhibit transplant rejection and to maintain inhibition of transplant rejection.

U.S. Pat. No. 5,212,155 issued to Calne et al. claims a combination of rapamycin and cyclosporine that is effective to inhibit transplant rejection.

U.S. Pat. No. 5,308,847 issued to Calne describes a combination of rapamycin and axathioprine to inhibit transplant rejection.

U.S. Pat. No. 5,403,833 issued to Calne et al. described a combination of rapamycin and a corticosteroid to inhibit transplant rejection.

U.S. Pat. No. 5,461,058 issued to Calne describes a combination of rapamycin and FK 506 to inhibit transplant rejection.

Published U.S. patent application Ser. No. US2001/0008888 describes a synergistic combination of IL-2 transcription inhibitor (e.g., cyclosporine A) and a derivative of rapamycin, which is useful in the treatment and prevention of transplant rejection and also certain autoimmune and inflammatory diseases, together with novel pharmaceutical compositions comprising an IL-2 transcription inhibitor in combination with rapamycin.

U.S. Pat. No. 6,239,124 issued to Zenke et al. also describes a synergistic combination of IL-2 transcription inhibitor and rapamycin which is useful in the treatment and prevention of transplant rejection and also certain autoimmune and inflammatory diseases, together with novel pharmaceutical compositions comprising an IL-2 transcription inhibitor in combination with rapamycin.

U.S. Pat. No. 6,051,596 issued to Badger describes a pharmaceutical composition containing a non-specific suppressor cell inducing compound and cyclosporine A in a pharmaceutically acceptable carrier. The patent also discloses a method of inducing an immunosuppressive effect in a mammal, which comprises administering an effective dose of the non-specific suppressor cell inducing compound and cyclosporine A to such mammal.

U.S. Pat. No. 6,046,328 issued to Schonharting et al. describes the preparation and combination of a Xanthine along with cyclosporine A or FK 506.

U.S. Pat. Nos. 5,286,730 and 5,286,731 issued to Caufield et al. describe the combination of rapamycin and cyclosporine A useful for treating skin diseases, and the delivery of the above compounds orally, parentally, intranasally, intrabronchially, topically, transdermally, or rectally.

Published International Application No. WO 98/18468 describes the synergistic composition comprising rapamycin and Calcitriol.

U.S. Pat. Nos. 5,624,946 and 5,688,824 issued to Williams et al. describe the use of Leflunomide to control and reverse chronic allograft rejection.

U.S. Pat. No. 5,496,832 issued to Armstrong et al. provides a method of treating cardiac inflammatory disease which comprises administering rapamycin orally, parenterally, intravascularly, intranasally, intrabronchially, transdermally or rectally.

As this prior art illustrates, the use of the combination of rapamycin and cyclosporine A in transplantation is known. The disclosed invention is distinct from the use of the combination in transplantations in that the rejection of an allograft does not does not involve injury to the recipients own vessels; it is a rejection type response. The disclosed invention is related to vascular injury to native blood vessels. The resulting intimal smooth muscle cell proliferation does not involve the immune system, but is growth factor mediated.

Accordingly, a need still exists for an improved therapeutic coating for an intravascular implant.

SUMMARY OF THE INVENTION

The present invention relates to an intravascular implant coating. The coating includes a therapeutically effective amount of a first agent, the first agent acting on a calcium independent cellular pathway, and, a therapeutically effective amount of a second agent, the second agent acting on a calcium dependent cellular pathway. The combined amount of the first and second agents treats or prevents hyperproliferative vascular disease.

In one embodiment, the first agent is a macrolide immunosuppressant, such as rapamycin, and the second agent is an IL-2 transcription inhibitor, such as cyclosporine A. The coating can contain a higher amount of rapamycin compared to cyclosporine A. The coating can be used on any type of implant. These include balloon catheters, stents, stent grafts, drug delivery catheters, atherectomy devices, filters, scaffolding devices, anastomotic clips, anastomotic bridges, and suture materials.

The coating can also include a polymer matrix, with the polymer being a resorbable polymer selected from the group consisting of poly-α hydroxy acids, polyglycols, polytyrosine carbonates, starch, gelatins, cellulose, and blends and co-polymers thereof. Examples of suitable poly-α hydroxy acids include polylactides, polyglycol acids, and blends and co-polymers thereof.

The coating can either be applied directly to the implant or on top of a primer layer upon which the coating is applied. The primer layer can be made of a resorbable polymer or a biostable polymer. If desired, a top coat can be applied over the coating. In one embodiment, the top coat is made of a resorbable polymer.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE EMBODIMENTS

In the description that follows, any reference to either orientation or direction is intended primarily for the convenience of description and is not intended in any way to limit the scope of the present invention thereto. Further, any reference to a particular biological application or implant, such as use of a stent for cardiovascular applications, is simply used for convenience as one example of a possible use for the invention and is not intended to limit the scope of the present invention thereto.

According to the present invention, a coating for an intravascular implant is provided. The coating can be applied either alone, or within a polymeric matrix, which can be biostable or bioabsorbable, to the surface of an intravascular device. The coating can be applied directed to the implant or on top of a polymeric substrate, i.e. a primer. If desired, a top coat can be applied to the therapeutic coating.

The intravascular implant coating according to the present invention comprises a therapeutically effective amount of a first agent, the first agent acting on a calcium independent cellular pathway, and a therapeutically effective amount of a second agent, the second agent acting on a calcium dependent cellular pathway. The combined amount of the first and second agents treats or prevents hyperproliferative vascular disease. In an exemplary embodiment, the first agent is rapamycin and the second agent is cyclosporine A.

Figure 1:
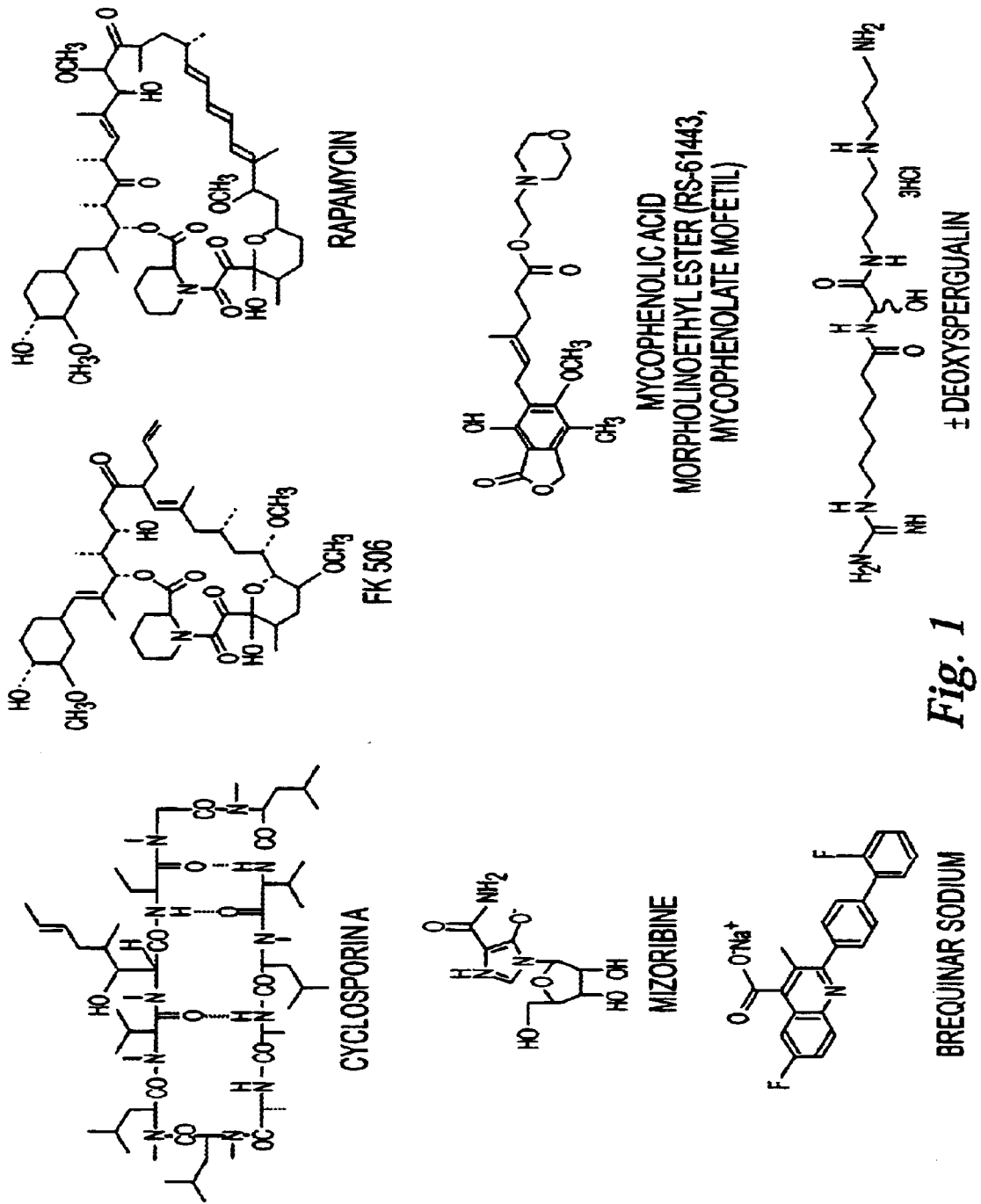
FIG. 1 shows the chemical structures of various macrocyclic immunosuppressants.

FIG. 1 shows the chemical structure of these and other agents. The distinct sites of action of rapamycin, which is a macrolide immunosuppressant acting on a calcium independent pathway, and cyclosporine A, which is an IL-2 transcription inhibitor acting on a calcium dependent pathway, and their relatively non-overlapping toxicities will enable this combination to be used intravascularly after angioplasty to prevent cellular growth at the site of injury inside the vessel.

Figure 4:
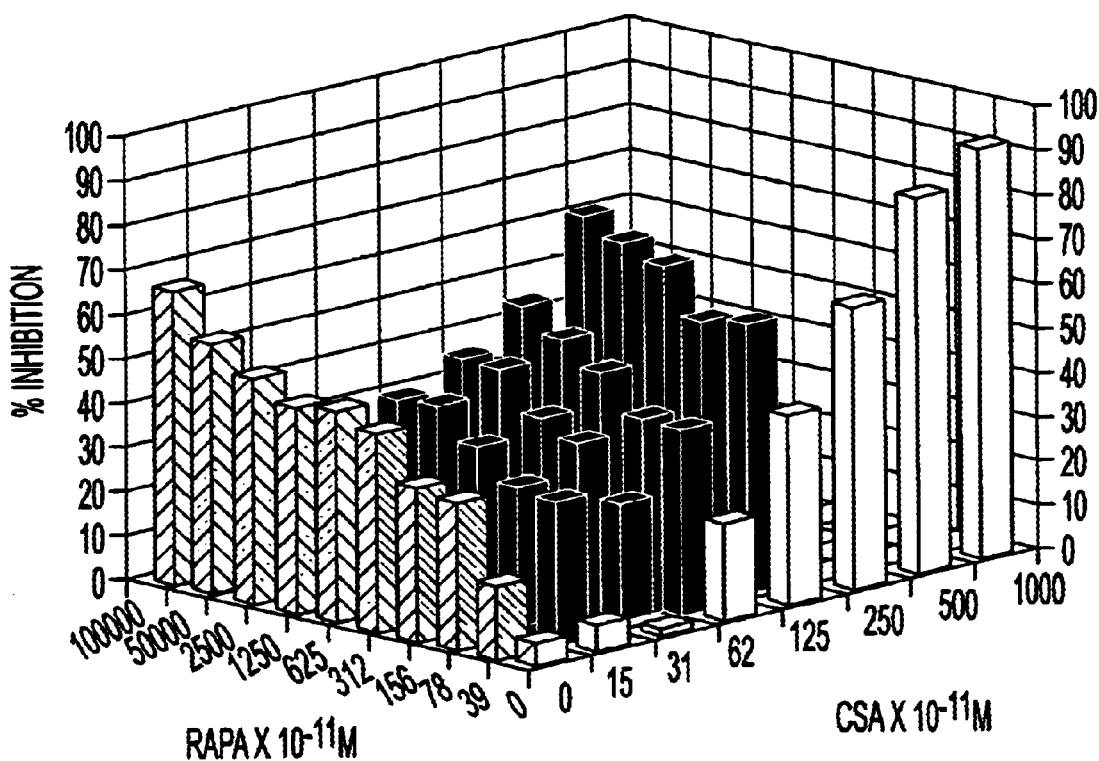
FIG. 4 shows a graph comparing the effects of cyclosporine A alone (white bars), rapamycin alone (hatched bars), and the combination of cyclosporine A and rapamycin (black bars) on the proliferative response of cells.

The rationale for a combinatorial therapy for intravascular therapy is at least in part as follows. The immunosuppressive efficacy to prevent allograft rejection after staggered administration of the two agents was similar to that obtained with simultaneous administration of combined therapy and significantly reduced the incidence of rejection in cardiac allografts (FIG. 4).

In the past, clinicians have learned to take advantage of known interactions, between cyclosporine A and other compounds such as "azole" antifungals to reduce cyclosporine A dose requirements. In particular, the azole antifungals have no known clinically significant immunosuppressive properties and have little toxicity at the doses used in this context. Because in this context, they are not given for their pharmocodynamic effects, the amount of absorption of the azole antifungals is not critical. In the case of co-administration of cyclosporine A and rapamycin, both agents have low and variable bioavailabilities as well as narrow therapeutic indices. In addition, this interaction is dose dependent and can be completely avoided with low doses of combinatorial delivery.

In some aspects, the process of allograft rejection is similar to the restenosis process inside the coronary arteries after injury to the vessel wall. After arterial, injury, multiple mitogenic and proliferative factors have been identified as capable of triggering signaling mechanisms leading to SMC activation. Numerous pharmacological agents, including antiplatelet agents, anticoagulants, ACE inhibitors, and cytotoxic agents have not significantly reduced restenosis after angioplasty. However because cyclosporine A and rapamycin inhibit multiple regulators of cell cycle progression in VSMCs, the mechanism of action differs from many of these agents. Because rapamycin and cyclosporine combination targets fundamental regulators of cell growth, it may significantly reduce restenosis.

A coating for an intravascular implant that includes the combination of rapamycin and cyclosporine A helps ensure that the mediation of cell growth happens very early in the cell cycle. For example, cyclosporine A acts early after T cell activation, thereby blocking transcriptional activation of early T cell specific genes. Rapamycin acts later in the cell cycle by blocking growth factor driven cell proliferation. The two agents can be provided in the coating such that the amount of rapamycin is higher than cyclosporine A. Thus, the ratio of rapamycin to cyclosporine A could be about 51% and above.

Figure 2:
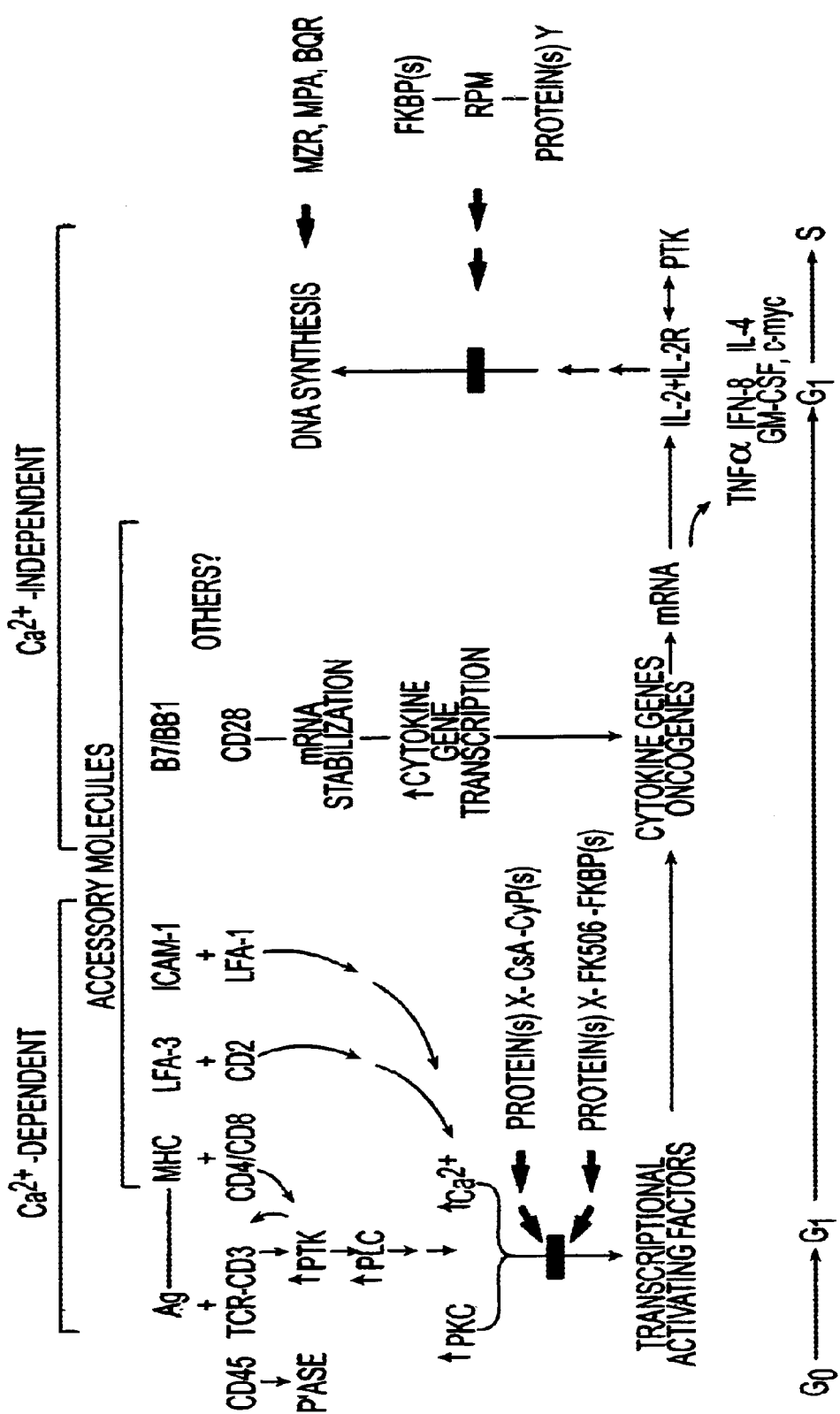
FIG. 2 shows a schematic of possible sites of action of cyclosporine A, FK 506, rapamycin, mizoribine, mycophenolic acid, brequinar sodium, and deoxyspergualin on T cell activation by calcium dependent or independent pathways. Certain immunosuppressants also affect B cells and their possible sites of action are also shown.
Figure 3:
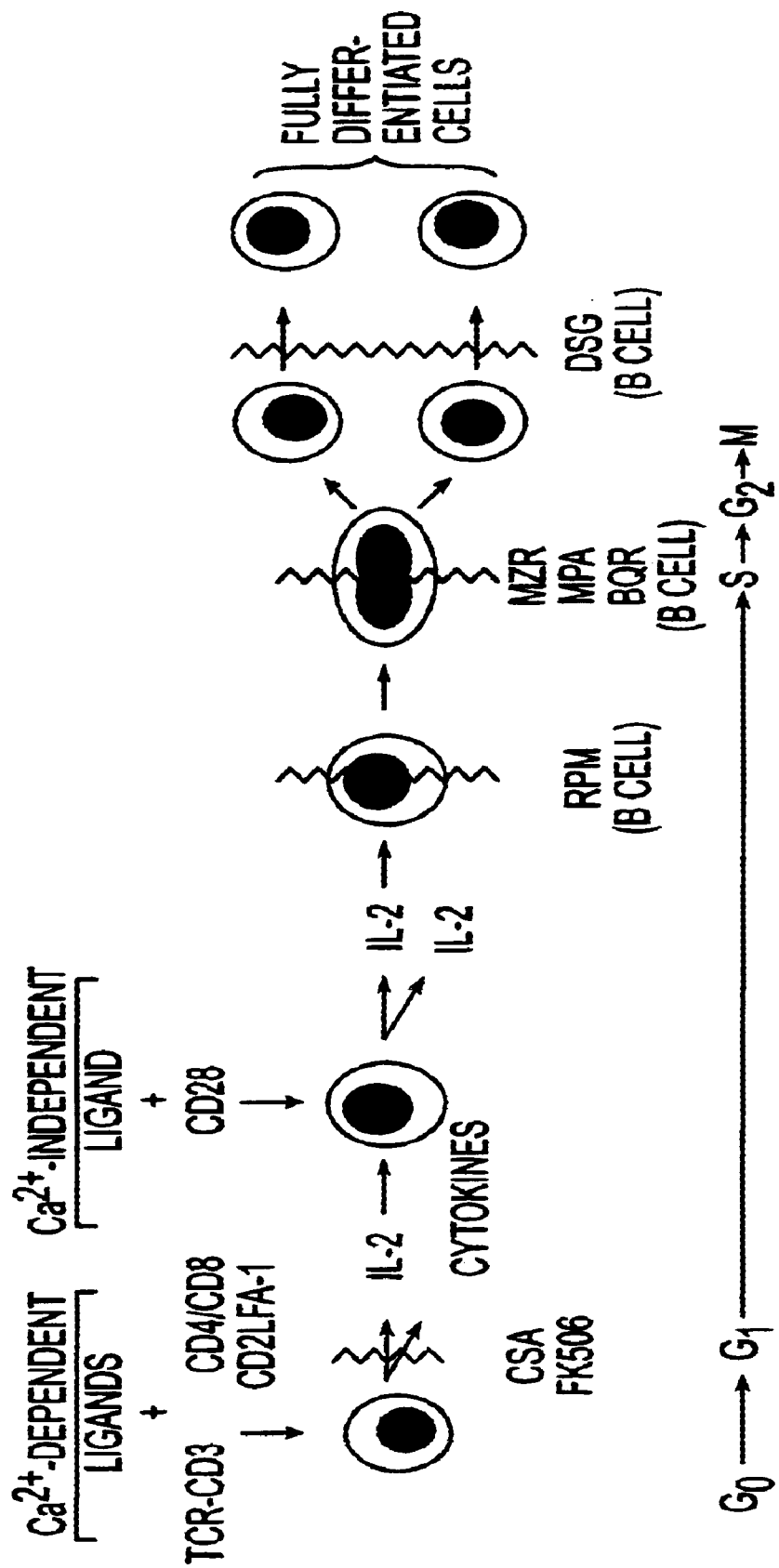
FIG. 3 shows a schematic of the effects of cyclosporine A, FK 506, rapamycin, mizoribine, mycophenolic acid, and brequinar sodium on the biochemistry of T cell activation.

As shown in FIGS. 2 and 3, the activation of T cells, which seems to be critical for induction of host resistance and consequent rejection of the transplanted organ, occurs in three phases. The first phase causes transcriptional activation of immediate and early genes (IL-2 receptor) that allow T cells to progress from a quiescent (G0) to a competent: (G1) state. In the second phase, T cells transduce the signal triggered by stimulating cytokines in both an autocrine and a paracrine fashion permitting entry into the cell cycle with resultant clonal expansion and acquisition of effector functions in the third phase of the immune response. While cyclosporine A inhibit the first phase and rapamycin inhibits the second phase of T cell activation. As of yet there is no available drug that acts on the third phase. By ensuring that the stent surface or any intravascular surface has both these drugs, it is ensured that the restenotic response from the arterial wall is significantly reduced or is completely eliminated.

Although the two agents could be used separately, a considerable over dosing has to be done to ensure that both the agents have a necessary therapeutic effect. This overdosing could potentially result in side effects, which include improper healing of the vessel and also an incomplete intimal formation.

Figure 5:
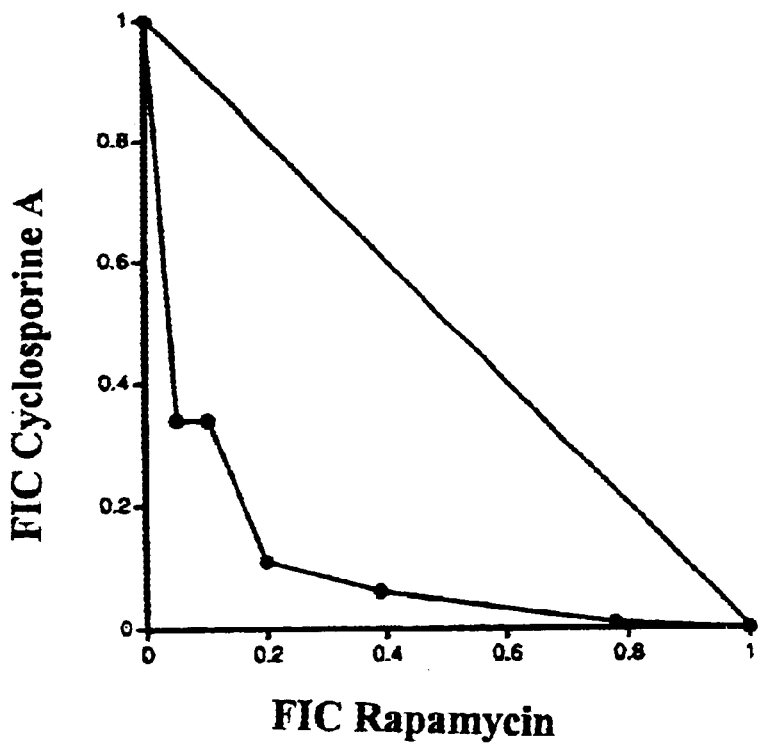
FIG. 5 shows an isobologram analysis of a combination of cyclosporine A and rapamycin. The line drawn from 1 to 1 is the line of unity. Combinations that fall below this unity line are synergistic, on the line additive, and above the line antagonistic. The units on the X-axis are Fractional Inhibitory Concentration (FIC) of rapamycin and the units on the Y-axis are FIC of cyclosporine A.
Figure 6:
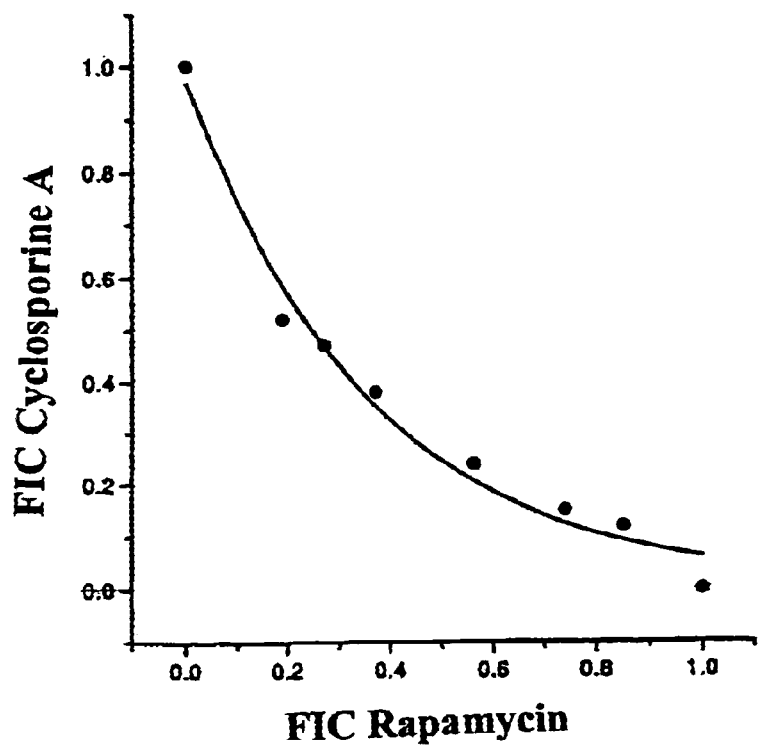
FIG. 6 shows an isobologram analysis of a combination of cyclosporine A and rapamycin. The units on the X-axis are FIC of rapamycin and the units on the Y-axis are FIC of cyclosporine A. The combination at which the maximum proliferative response was inhibited was used to plot the synergistic interaction between the two.

The combination of the agents would mean that both agents can be combined at a very low dosage and the combination would actually increase the therapeutic levels rather than administering monotherapy. This is illustrated in FIGS. 5 and 6, which shows the synergistic effects of rapamycin and cyclosporine A. The toxicity of the combination of agents is significantly reduced when both are combined together. Providing two agents that are active on two different cell cycles to prevent proliferation increases the therapeutic window of the agent. The combination actually increases the level of immunosuppression when compared to monotherapy.

It should be noted that the present invention relates to a combinatorial therapy for delivery of more than one agent through a coating on any intravascular implant. As used herein, implant means any type of medical or surgical implement, whether temporary or permanent. Delivery can be either during or after an interventional procedure. Non-limiting examples of intravascular implants now follow.

The outside surface of a balloon catheter may be coated with the combination according to the present invention and could be released immediately or in a time dependent fashion. When the balloon expands and the wall of the vessel is in contact with the balloon, the release of the combination can begin. Small nanospheres of the agents can actually be transported into the vessel wall using the balloon so that these nanospheres ensure delivery over longer period of time.

The surface of a stent may be coated with the combination of agents and the stent is implanted inside the body. The stent struts could be loaded with several layers of the agents or with just a single layer. A transporter or a vehicle to load the agents on to the surface can also be applied to the stent. The graft material of the stent graft can also be coated (in addition to the stent or as an alternative) so that the material is transported intravascularly at the site of the location or the injury.

The drug delivery catheters that are used to inject drugs and other agents intravascularly can also be used to deliver the combination of agents. Other intravascular devices through which the transport can happen include atherectomy devices, filters, scaffolding devices, anastomotic clips, anastomotic bridges, suture materials etc.

The present invention envisions applying the coating directly to the intravascular implant. However, the coating can be applied to a primer, i.e. a layer or film of material upon which another coating is applied. Furthermore, the first and second agents can be incorporated in a polymer matrix. Polymeric matrices (resorbable and biostable) can be used for delivery of the therapeutic agents. In some situations, when the agents are loaded on to the implant, there is a risk of quick erosion of the therapeutic agents either during the expansion process or during the phase during with the blood flow is at high shear rates at the time of implantation. In order to ensure that the therapeutic window of the agents is prolonged over extended periods of time, polymer matrices can be used.

These polymers could be any one of the following: semitelechelic polymers for drug delivery, thermo responsive polymeric micelles for targeted drug delivery, pH or temperature sensitive polymers for drug delivery, peptide and protein based drug delivery, water insoluble drug complex drug delivery matrices polychelating amphiphilic polymers for drug delivery, bioconjugation of biodegradable poly lactic/glycolic acid for delivery, elastin mimetic protein networks for delivery, generically engineered protein domains for drug delivery, superporbus hydrogel composites for drug delivery, interpenetrating polymeric networks for drug delivery, hyaluronic acid based delivery of drugs, photocrosslinked polyanhydrides with controlled hydrolytic delivery, cytokine-inducing macromolecular glycolipids based delivery, cationic polysaccharides for topical delivery, n-halamine polymer coatings for drug delivery, dextran based coatings for drug delivery, fluorescent molecules for drug delivery, self-etching polymerization initiating primes for drug delivery, and bioactive composites based drug delivery.

Regardless of whether the coating includes a polymer matrix and where it is applied (directly on the implant, on top of a primer, or covered with a top coat), there are a number of different methods for applying the therapeutic coating according to the present invention. These include dip coating and spray coating. Applicant's co-pending application entitled "Process for Coating a Surface of a Stent", filed on even date with respect to the instant application, discusses prior art with respect to coating processes and discloses a novel method for coating a stent. The entire disclosure of this co-pending application is incorporated herein reference.

Another process for applying the therapeutic coating to an intravascular implant, in this case a stent, is as follows:

1. The stent is laser cut and then electropolished

2. The electropolished stent is cleaned in a 1%–5% W/V Potassium hydroxide or Sodium hydroxide for 1 hour. The temperature may be elevated to about 60 C to ensure proper cleaning. The cleaning can also be done with hexane or a solution of isopropyl alcohol.

3. The device is then washed with hot water. The washing may take place in a bath in which water is maintained at a constant temperature. Alternatively, the hot water is maintained on top of an ultrasonic bath so that the stent swirls as it is cleaned in the hot water.

4. The stent is dried at room temperature for up to 4 hours.

5. A primer is applied to the stent. The primer prepares the surface of the stent for the subsequent stages of bonding to the polymer.

6. Prepare functionalization chemicals. These chemicals could include hydride terminated polyphenyl_ (dimethylrosiloxy) siloxanes; methylhydrosiloxane, phenylmethylsiloxane and methylhydrosiloxane-octylmethylsiloxane copolymers, hydride terminated polydimethylsiloxanes, methylhydrosiloxane-dimethylsiloxane copolymers; polymethylhyrosiloxanes, polyethylhydrosiloxanes. The chemicals could also include silanol functional siloxanes, like silanol terminated polydimethylsiloxanes; silanol terminated diphenylsiloxane-dimethylsiloxane copolymers; and silanol terminated polydiphenylsiloxanes. Suitable epoxy functional siloxanes include epoxy functional siloxanes include epoxypropoxypropyl terminated polydimethylsiloxanes and (epoxycyclohexylethyl) methylsiloxane-dimethylsiloxane copolymers.

7. The agents can be incorporated in the mixture of the polymer solution or can be bonded on to the surface of the polymer and also could be grafted on to the surface. One or more of the therapeutic agents is mixed with the coating polymers in a coating mixture. The therapeutic agent may be present as a liquid, a finely divided solid, or any other appropriate physical form. The mixture may include one or more additives, nontoxic auxiliary substances such as diluents, carriers, stabilizers etc. The best conditions are when the polymer and the drug have a common solvent. This provides a wet coating, which is a true solution.

8. The device is then place in a mixture of functionalization chemicals for 2 hours at room temperature. An oscillating motion as described in the above-identified co-pending patent application can facilitate the coating process.

9. The device is then washed with methanol to remove any surface contaminants.

10. If there is a top coat of polymeric material that encapsulates the complete drug-polymer system, then the top coat is applied to the stent. The top coat can delay the release of the pharmaceutical agent, or it could be used as a matrix for the delivery of a different pharmaceutically active material.

11. The total thickness of the undercoat does not exceed 5 microns and the top coat is usually less than 2 microns.

While various descriptions of the present invention are described above, it should be understood that the various features could be used singly or in any combination thereof. Therefore, this invention is not to be limited to only the specifically preferred embodiments depicted herein.

Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. An intravascular implant coating comprising:
   a therapeutically effective amount of a first agent, the first agent acting on a calcium independent cellular pathway; and
   a therapeutically effective amount of a second agent, the second agent acting on a calcium dependent cellular pathway,
   wherein the combined amount of the first and second agents treats or prevents hyperproliferative vascular disease and wherein the first agent is a macrolide immunosuppressant and the second agent is an IL-2 transcription inhibitor.

2. The coating of claim 1 wherein the first agent is rapamycin.

3. The coating of claim 1 wherein the second agent is cyclosporine A.

4. The coating of claim 1 wherein the first agent is rapamycin and the second agent is cyclosporine A.

5. The coating of claim 4 in the coating contains a higher amount of rapamycin than cyclosporine A.

6. The coating of claim 1 wherein the intravascular implant is selected from the group consisting of balloon catheters, stents, stent grafts, drug delivery catheters, atherectomy devices, filters, scaffolding devices, anastomotic clips, anastomotic bridges, and suture materials.

7. The coating of claim 1 wherein the coating includes a polymer matrix.

8. The coating of claim 7 wherein the polymer matrix includes a resorbable polymer.

9. The coating of claim 1 wherein the intravascular implant includes a primer layer upon which the coating is applied.

10. The coating of claim 9 wherein the primer layer is made of a resorbable polymer.

11. The coating of claim 9 wherein the primer layer is made of a biostable polymer.

12. The coating of claim 1 wherein a top coat is applied over the coating.

13. The coating of claim 12 wherein the top coat is made of a resorbable polymer.

14. An intravascular implant coating comprising:
   a therapeutically effective amount of rapamycin; and
   a therapeutically effective amount of cyclosporine A,
   wherein the combined amount of rapamycin and cyclosporine A treats or prevents hyperproliferative vascular disease.

15. The coating of claim 14 wherein the coating further includes a resorbable polymer matrix, with the rapamycin and cyclosporine A dispersed within the resorbable polymer matrix.

16. The coating of claim 15 wherein the resorbable polymer matrix is selected from the group consisting of poly-α hydroxy acids, polyglycols, polytyrosine carbonates, starch, gelatins, cellulose, and blends and co-polymers thereof.

17. The coating of claim 16 wherein the resorbable polymer matrix includes poly-α hydroxy acids that are selected from the group consisting of polylactides, polyglycol acids, and blends and co-polymers thereof.

18. The coating of claim 14 wherein the coating contains a higher amount of rapamycin than cyclosporine A.

19. The coating of claim 14 wherein the coating includes a polymer matrix.

20. The coating of claim 19 wherein the polymer matrix includes a resorbable polymer.

21. The coating of claim 14 wherein the intravascular implant includes a primer layer upon which the coating is applied.

22. The coating of claim 21 wherein the primer layer is made of a resorbable polymer.

23. The coating of claim 21 wherein the primer layer is made of a biostable polymer.

24. The coating of claim 14 wherein a top coat is applied over the coating.

25. The coating of claim 24 wherein the top coat is made of a resorbable polymer.

* * * * *